United States Patent [19]

Aleck

[11] 4,232,554
[45] Nov. 11, 1980

[54] THERMAL EMISSION FLAW DETECTION METHOD

[75] Inventor: Benjamin J. Aleck, Jackson Heights, N.Y.

[73] Assignee: Grumman Aerospace Corporation, Bethpage, N.Y.

[21] Appl. No.: 964,912

[22] Filed: Nov. 30, 1978

[51] Int. Cl.³ ............................................. G01N 3/32
[52] U.S. Cl. ...................................... 73/577; 73/104; 73/355 R; 73/356; 73/762; 73/799; 73/805
[58] Field of Search ............... 73/762, 799, 805, 808, 73/577, 356, 15 FD, 15.6, 104, 355, 811, 812

[56] References Cited

U.S. PATENT DOCUMENTS

| | | |
|---|---|---|
| 1,680,589 | 8/1928 | Bock . |
| 3,168,825 | 2/1965 | Prochazka .......................... 73/812 |
| 3,511,086 | 5/1970 | Woodmansee ....................... 73/104 |
| 3,596,519 | 8/1971 | Blonder et al. ..................... 73/355 |

OTHER PUBLICATIONS

Rice, J. R. et al., *Local Heating by Plastic Deformation at a Crack Tip*, in The Physics of strength and plasticity, ed by Agon, M.I.T. Press Cambridge 1969.
Charles, J. A., et al., "Using the Scanning Infrared Camera in Experimental Fatique Studies", *Experimental Mechanics*, 15(4) 133-138.

*Primary Examiner*—S. Clement Swisher
*Attorney, Agent, or Firm*—Morgan, Finnegan, Pine, Foley & Lee

[57] ABSTRACT

A method of detecting very small structural flaws at loads below those which cause the flaws to propagate is disclosed. Certain phenomena and relationships of fracture mechanics are utilized in conjunction with the generation, detection and interpretation of thermal emission signals indicative of plastic deformation of the tested material.

9 Claims, 3 Drawing Figures

UNIFORM, TENSILE STRESS (NORMAL TO CRACK)

$K = \sigma\sqrt{\pi a}$

THERMAL EMISSION FLAW DETECTION METHOD

BACKGROUND OF THE INVENTION

This invention relates to an improved method for nondestructively detecting even very small flaws in a structure. More specifically, it relates to the application of certain phenomena and relationships of fracture mechanics to the generation, detection and interpretation of thermal emission signals emitted by the material comprising the structure undergoing testing.

Almost all structural failures are caused by fatigue, brittle fracture, plastic failure, creep, instability or corrosion. Approximately 90% of all service failures are caused by fatigue flaws.

Fatigue is typically defined as a failure engendered by stress variation attending cyclical loading of the structure. In practice the stress variation may be periodic as with rotating structure such as turbine blades or aperiodic as in the case of an aircraft wing. Structures such as turbine blades may be designed with great fatigue life having, for example, a service life as high as $10^{12}$ stress cycles. Other structures such as glass-filament wound rocket motor cases are designed to experience fatigue failure if exposed to a relatively few stress cycles.

Fatigue strength is often expressed in terms of S-N curves which are coordinate plots of stress amplitude (S) and number of cycles to failure (N). More materials such as steel commonly exhibit an endurance limit. If stress amplitude is maintained below the limit, fatigue failure will not occur. For other types of materials, the test data thus far available do not indicate that an endurance limit exists. For many applications the expected use involves far fewer than $10^8$ cycles. The engineers then treat the stress amplitude at $10^8$ cycles as a nominal endurance limit.

Whereas in many materials fracture under static loading conditions is generally preceded by readily detectable bulk plastic deformation, no such obvious indications usually signal impending fatigue fracture. Typically a microscopic flaw or crack is formed at a localized point of stress concentration. Under cyclic load the flaw becomes a fatigue flaw. Once formed, the fatigue flaw grows with each continued load cycle. Ultimately a point is reached at which unstable growth occurs, thereby resulting in catastrophic fracture.

Fatigue strength is a complex function of many variables including a spectrum of stress amplitudes, corresponding number of stress-cycles, nature of the applied stress, type of structure and surface conditions.

Almost invariably, the local microscopic stress concentration points at which the onset of fatigue occurs are produced at material, design, manufacturing or corrosion induced discontinuities, such as welds, cutouts, rivet holes, notches, or at voids, scratches, tool marks or other defects.

One type of flaw detection technique which depends upon cyclic loading is acoustic emission. The measured signal depends upon the tearing sounds associated with flaw growth. However, by the time a flaw has propagated sufficiently for detection, the useful life of the structure being tested may have been materially shortened. Thus, in many high reliability applications the effect of flaw propagation in conjunction with structural testing is clearly undesirable.

Illustrative examples of high reliability applications where the effect of flaw propagation in conjunction with structural testing is undesirable may be found in the aerospace industry. One such important area pertains to the ability to determine, as part of a Quality Control incoming inspection procedure, whether certain expensive high reliability structural components, such as jet engine blades and hydraulic tubing, are flawed prior to installation in the aircraft. The ability to detect flaws prior to installation enhances the operational reliability of the aircraft and avoids the unnecessary expense associated with the installation and subsequent removal of the flawed components. Similarly, the ability to accurately predict residual life, particularly where an aircraft or engine component might have reached its specified life, but may not have endured the loading it was designed to survive, is an important area for application of nondestructive testing methods.

It is apparent that one of the limitations of the acoustic emission flaw detection technique is its inherent dependency upon flaw growth. In the testing of high reliability component structures this is clearly undesirable, since the resulting flaw propagation may appreciably shorten the useful life of the structure being tested.

Accordingly, it is an object of the invention to provide an improved method for nondestructively detecting even very small flaws in a structure. More specifically, it is an object of the invention to overcome the aforementioned limitations associated with the acoustic emission flaw detection technique.

It is a further object of the invention to provide a nondestructive thermal emission flaw detection method.

SUMMARY OF THE INVENTION

The foregoing and other objects and advantages which will be apparent in the following detailed description of the preferred embodiment, or in the practice of the invention, are achieved by the invention disclosed herein, which generally may be characterized as a nondestructive method for detecting flaws in a structure comprising a material having a characteristic threshold stress intensity factor, including the steps of:
 (a) loading the structure at a level corresponding to a stress intensity factor below the characteristic threshold stress intensity factor of the material; and
 (b) positioning detection means in thermal proximity to the structure for detecting thermal emission signals indicative of plastic deformation.

DESCRIPTION OF PREFERRED EMBODIMENT

In order to afford a complete understanding of the invention and an appreciation of its advantages, a description of a preferred embodiment in a typical operating environment is presented below.

Thermal emission is a novel nondestructive method of flaw detection predicated on the heating which occurs at the tip of a sharp flaw when that flaw is cyclically loaded. The heat is generated by cyclic plastic deformation which occurs at the small plastic zone surrounding the tip of the flaw. In general, the resulting increase in temperature varies as the cyclic frequency; is proportional to the volume of the plastic zone; and is inversely proportional to the thermal conductivity of the material. Typically, the radius of the heated zone decreases with increased convective cooling; increases with thermal conductivity; and increases with material thickness.

Application of certain phenomena and relationships of fracture mechanics to the generation, detection and interpretation of thermal emission signals results in a method for detecting very small sharp flaws in a nondestructive manner. A sharp flaw is one which has a tip radius approaching zero, such as exhibited by fatigue induced flaws, and a very small flaw is one which is not detectable by conventional nondestructive testing techniques (NDT).

Typically, a flaw less than 0.005" in depth gives rise to a measurable increase in temperature in a heated zone about 0.5" in diameter. Flaws of this size are usually not detectable by conventional nondestructive testing methods. However, utilizing thermal emission techniques, detectable signals corresponding to flaws of this size are obtained at loads below those which cause the flaw to propagate.

As will be discussed below, the use of thermal emission signals in conjunction with certain phenomena and relationships of fracture mechanics permits evaluation of the severity of very small sharp flaws in a nondestructive manner and also allows a prediction of the rate of flaw propagation under cyclic load.

To better understand and appreciate the present invention and its advantages, it is helpful to understand, in general, certain phenomena and relationships of fracture mechanics.

Fracture mechanics concepts are particularly useful in the analysis of the fracture strength of aircraft structures. The basic unit of fracture mechanics is the stress intensity factor K. In general, K is a function of the geometry of the structure, the loading condition, and the geometry of the flaw. When the value of K is divided by the square root of the radius from the tip of the flaw, the result is the maximum stress at that distance from the flaw tip. Once known, K may be used in determining the rate of flaw growth per cycle of applied load.

Figure 1:
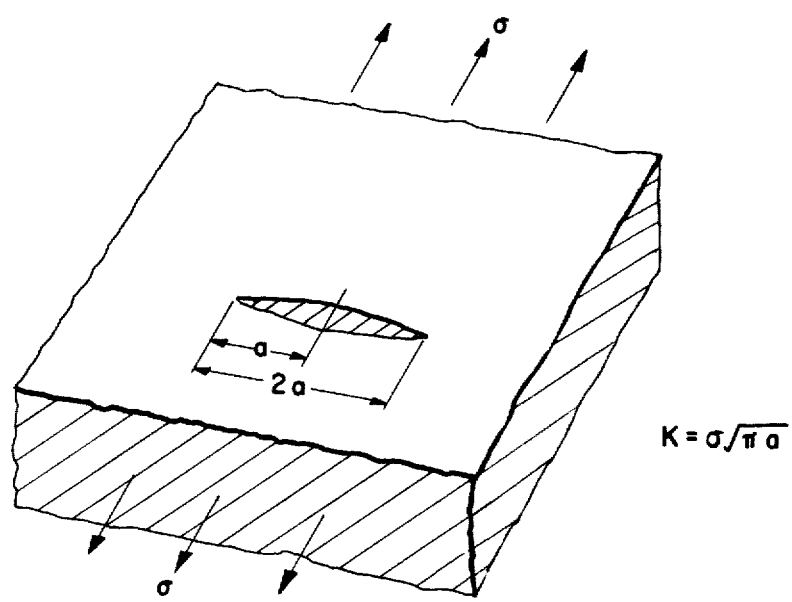
FIG. 1 illustrates a through-the-thickness flaw in a wide panel.

To illustrate the utility of the value of K, a wide panel under uniform tensile load with a through-the-thickness flaw of width $2a$ is depicted in FIG. 1.

Referring now to FIG. 1, the stress intensity factor K for this type of loading is readily derived by one skilled in the art, and is represented by the following equation:

$$K = \sigma \sqrt{\pi a}$$

where
 $\sigma$ = tensile stress; and
 a = half-width of the flaw.

It is observed that the value of K in the above equation is expressed in the units of stress times the square root of inches. Accordingly, when K is divided by the square root of the radius from the flaw tip the resulting quantity is expressed in terms of units of stress, i.e., the stress at that radius.

Figure 2:
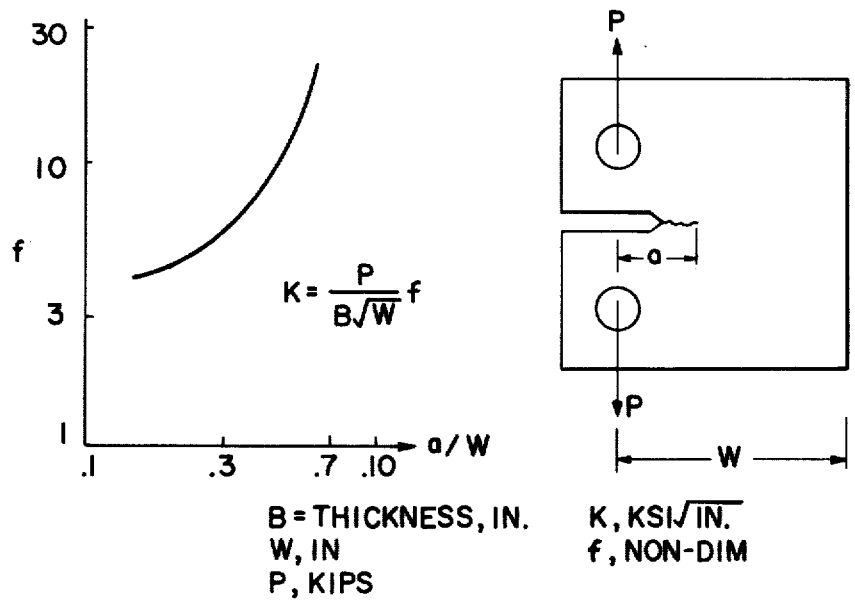
FIG. 2 illustrates a through-the-thickness flaw in a compact tensile coupon.

The compact tensile coupon depicted in FIG. 2 is also illustrative from the fracture mechanics point of view.

Referring now to FIG. 2, a coupon comprising a flat plate with two circular holes for applying loads is illustrated. As shown therein, a flaw, created, for example, with a saw cut, is located midway between the two holes. Under cyclic load the flaw becomes a fatigue flaw. The length of the flaw, a, is the distance from the centerline of the holes to the end of the fatigue flaw. W represents the full width of the specimen and B its thickness. The stress intensity factor K for this type of loading is readily derived by one skilled in the art, and is represented by the following equation:

$$K = \frac{P}{B\sqrt{W}} f$$

where
 a = length of the fatigue flaw;
 P = applied load;
 B = thickness;
 W = width; and
 f = f(a/W).

The value of f for a given value of a/W is accurately known. Approximate values can be read off the plot in FIG. 2.

When the coupon illustrated in FIG. 2 is utilized to grow a flaw under constant amplitude of cyclic loading, the flaw length, a, and the number of cycles, N, to achieve that flaw length are noted. Since a is growing, K will be growing and a complete picture of the da/dN versus K curve will be generated. The value of da/dN, the slope of the curve, as a function of the value of K is readily determined.

Figure 3:
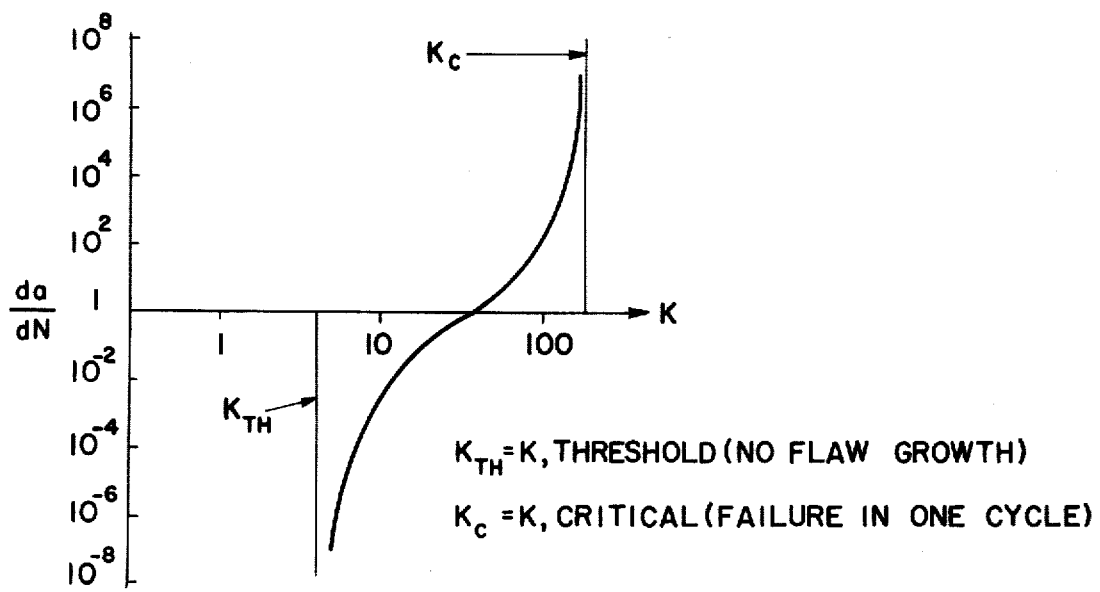
FIG. 3 is a graphical representation of a typical flaw growth rate versus cyclic K value curve.

FIG. 3 illustrates a typical plot of flaw growth rate, da/dN, versus stress intensity factor K.

Referring now to FIG. 3, it is observed that the curve depicted has two asymptotes. The left asymptote is called K threshold, $K_{TH}$, and the right asymptote is called K critical, $K_C$. At a value of K equal to $K_C$, the structure will fail in one cycle of loading. At a value of K less than $K_{TH}$, flaw growth will not occur. It is apparent that if one wishes to use thermal emission as a nondestructive means of flaw detection, loads corresponding to K's less than $K_{TH}$ must be utilized to ensure that the flaw does not propagate under cyclic loading. For materials of interest such as D6Ac steel and Ti-6Al-4V titanium alloy, $K_{TH}$ is approximately 6 ksi $\sqrt{in}$.

If the flaw is not growing, a steady state temperature distribution results. In this case, the relationship between thermal emission, $\Delta T$, and stress intensity factor, K, for a through-the-thickness flaw, is readily derived by one skilled in the art, and as a first order approximation, is represented by the following equation:

$$\Delta T = \frac{C(\sigma_y \epsilon_p)(\Delta K)^4 f}{k}$$

where
 $\Delta T$ = increase in temperature above ambient;
 C = a constant;
 $\sigma y$ = yeild point of the material;
 $\epsilon p$ = plastic strain imposed;
 $\Delta K$ = change in the value of K when $P_{max}$ and $P_{min}$ are applied;
 f = load frequency; and
 k = thermal conductivity.

Assuming that the means value of ($\sigma y \epsilon p$) does not change with plastic zone size, and that the testing is done at a constant frequency, the above equation reduces to:

$$\Delta T = C_1(\Delta K)^4.$$

Surface flaws are the most common type of flaw. Using data developed for through-the-thickness flaws, it is possible to utilize thermal emission signals from surface flaws to evaluate the flaw severity. Assuming an initially shallow surface flaw of width 2C and depth a, the value of K surface flaw, $K_{SF}$, for a given stress level is available in the literature. Assuming that the heat generated per cycle is approximately constant along the length of the surface flaw, first-order approximations represented by the following equations are readily derived by one skilled in the art based upon the assumption of zero temperature gradient through the thickness:

$$(\Delta T)_{SF} = (\Delta T)_{TT} \times \frac{2C}{B}$$

$$R_{SF} = R_{TT} \times \frac{2C}{B}$$

where
$\Delta T$ = increase in temperature above ambient;
SF = surface flaw;
TT = through-the-thickness flaw;
2C = flaw width;
B = thickness; and
R = radius of heated zone.

To obtain the maximum thermal emission signal at the lowest possible cycle load amplitude, it is desirable to test at the highest practical frequency. One means of reducing the size of the loading equipment is to test the structure at a resonant frequency. The loading system and the structure comprise a combined mass and spring system having readily determined resonant frequencies. Utilizing conventional resonance techniques, it may be possible to create an effective load 25 times as large as the applied load. The type of resonant loading need not be that normally applied in use, so long as it achieves the desired level of stress at the points of interest.

Theoretically, all materials which exhibit plastic deformation will produce thermal emissions. However, as observed above, the magnitude of the thermal emission signals varies inversely with the thermal conductivity of the material comprising the structure being tested. Accordingly, to detect thermal emissions from a good heat conductor such as aluminum or copper requires the use of a sensitive heat sensor. Using present-day equipment it is possible to sense thermal emission signals corresponding to an increase in local temperature on the order of 0.1° F.

One technique for sensing an increase in local temperature at the tip of cyclically loaded flaw utilizes cholesteric liquid crystals positioned in thermal proximity to the structure being tested. The liquid crystals may consist, for example, of F-80 film manufactured by Robert Parker Associates. Typically, the liquid crystals, which are calibrated against a known standard, are bonded to the structure being tested to maintain a thermally responsive contact. To enhance bonding of the liquid crystals to the test structure, the liquid crystals are deposited on a clear plastic (Mylar) sheet, having a thickness typically on the order of 5 mils, the rear surface of which may be gum backed. Since liquid crystals experience a sequence of color transitions at specific temperatures, it may be necessary to raise the local ambient to the temperature at which the first color transition would appear. A uniform color ensures that the surface temperature distribution is sufficiently uniform. If testing in a drafty area, a leaky enclosure may be adequate to cut off most air currents so that the ambient temperature changes slowly.

Another technique for sensing an increase in local temperature at the tip of a cyclically loaded flaw makes use of a scanning infrared detector, such as, for example, the AGA Thermovision camera, positioned in thermal proximity to the structure being tested. The basic advantage of the scanning infrared detector is that the same or better sensitivity is achieved over a wider range of temperatures without the necessity of controlling the ambient temperature, which is the instrument's reference temperature, or mounting a coating on the surface of the test structure.

To illustrate the application of certain phenomena and relationships of fracture mechanics discussed above to the generation, detection and interpretation of thermal emission signals, a nondestructive method for detecting flaws in a jet engine compressor blade comprising a titanium alloy will now be discussed. The blade to be tested is mounted to a conventional test fixture such as, for example, a shake table. Commercially available liquid crystals are positioned on one surface of the blade. It is not necessary to monitor both sides of the blade with liquid crystals, since the blades are thin and the heat generated will readily flow from one surface to the other. The F-80 liquid crystals experience a sequence of color transitions commencing at temperatures slightly above 80° F. Small increases in temperature above this point cause the crystals to undergo a sequence of color transitions from black to straw to green to blue and then back to black again, at about 82° F. Since the heat generated by the test fixture may exceed 80° F., it may be necessary to remove any excess heat by, for example, flowing coolant through the test fixture. The coolant flow is adjusted to bring the liquid crystals to a uniform straw color all along the blade. To ensure that flaw propagation does not occur under cyclic loading conditions, it is necessary to maintain the value of the applied stress intensity factor K at a level below the characteristic threshold stress intensity $K_{TH}$ for titanium alloy. This is accomplished by gradually increasing the amplitude of vibration until local heating effects, as evidenced, for example, by the color transition from straw to green, are observed. Typically, this color transition corresponds to an increase in temperature on the order of 0.5° F. From previous calculations and the $\Delta T$ versus K plot for titanium alloy, it is known that an increase in temperature on the order of 0.5° F. corresponds to a K level well below $K_{TH}$. The regions at which the color transitions occur indicate the location of flaws. Once the location of a flaw is determined several additional observations concerning the character and extent of the flaw are made. Typically, a conventional dye check is made to determine the detectable flaw lengths on both surfaces. For a surface flaw only one length will be measurable.

If the flaw is a through-the-thickness type, the measured increase in temperature $\Delta T$ can be directly converted to a K value, from the K versus $\Delta T$ curve characteristic of titanium alloy. Since the applied stress, $\sigma$, is easily determined using conventional stress-analysis techniques, the depth of the flaw, a, is readily calculated from the equation $K = \sigma\sqrt{\pi a}\, f$, where f depends on the geometry and loading conditions.

If the flaw is a surface flaw its width 2C and thickness B must be measured. Inserting the measured quantities 2C, B and $\Delta T_{SF}$ into the equation $$\Delta T_{SF} = \Delta T_{TT} \times \frac{2C}{B}$$

allows the value of $\Delta T_{TT}$ to be computed. Once $\Delta T_{TT}$ is known, the K versus $\Delta T_{TT}$ curve characteristics of titanium alloy, is used with the appropriate K formula to calculate the depth of the flaw, a.

Having determined the severity of the flaw by calculating its depth, a, it is now possible to predict the residual life of the flawed structure by using the characteristic da/dN versus K curve for titanium alloy.

The technique described above was utilized to verify a fatigue flaw cycled at 300 Hz. A green zone 1" in diameter on a straw background was centered on the flaw in a 1" diameter titanium alloy tube of 0.070" thickness. Even laboratory NDT techniques could not find the flaw, even though its location was marked. It is projected that for titanium alloy parts it will be possible to detect surface flaws as small as 0.010" long by 0.005" deep using thermal emission techniques. Flaws this small are admittedly undetectable by other present day techniques.

The nondestructive method discussed above is also applicable in the case of an applied load which is noncyclic. However, because a steady state temperature distribution is not achieved, it may be necessary to utilize more sensitive detection means to sense an increase in local temperature at the tip of a flaw. Illustrative examples of noncyclic loading conditions are drop tests and explosive tests.

Under certain conditions, it may be desired to terminate a test once a flaw is detected. The output of a conventional electro-optical threshold measurement system may be used to trigger indicating means such as, for example, a flasher or buzzer to produce an appropriate signal indicating that a flaw has been detected and the test should be terminated. Alternatively, the output of a conventional electro-optical threshold measurement system may be used to produce a voltage level which in turn is utilized to activate a switch or relay to produce an appropriate shut-down signal indicating the detection of a flaw.

It is clear that the above description of the preferred embodiment in no way limits the scope of the present invention which is defined by the following claims.

What is claimed is:

1. A nondestructive method for detecting flaws in a structure comprising a material having a characteristic threshold stress intensity factor, including the steps of:
   (a) loading the structure at a level corresponding to a stress intensity factor below the characteristic threshold stress intensity factor of the material; and
   (b) positioning detection means in thermal proximity to the structure for detecting thermal emission signals indicative of plastic deformation.

2. The method of claim 1 further including the step of determining the positioning of the detection means by measuring and observing the detected thermal emission signals until a region is located on the surface of the structure where the measured thermal emission signals exceed a predetermined level.

3. The method of claim 2 including the additional step of producing a signal responsive to said detection means indicating that said detected thermal emission signals exceed a predetermined level.

4. A nondestructive method for detecting flaws in a structure comprising a material having a characteristic threshold stress intensity factor, including the steps of:
   (a) cyclically loading the structure at a level corresponding to a stress intensity factor below the characteristic threshold stress intensity factor of the material; and
   (b) positioning detection means in thermal proximity to the structure for detecting thermal emission signals indicative of plastic deformation.

5. The method of claim 4 further including the step of determining the positioning of the detection means by measuring and observing the detected thermal emission signals until a region is located on the surface of the structure where the measured thermal emission signals exceed a predetermined level.

6. The method of claim 5 including the additional step of producing a signal responsive to said detection means indicating that said detected thermal emission signals exceed a predetermined level.

7. A nondestructive method for detecting flaws in a structure comprising a material having a characteristic threshold stress intensity factor, including the steps of:
   (a) resonantly loading the structure;
   (b) cyclically loading the structure at a level corresponding to a stress intensity factor below the characteristic threshold stress intensity factor of the material; and
   (c) positioning detection means in thermal proximity to the structure for detecting thermal emission signals indicative of plastic deformation.

8. The method of claim 7 further including the step of determining the positioning of the detection means by measuring and observing the detected thermal emission signals until a region is located on the surface of the structure where the measured thermal emission signals exceed a predetermined level.

9. The method of claim 8 including the additional step of producing a signal responsive to said detection means indicating that said detected thermal emission signals exceed a predetermined level.

* * * * *